United States Patent [19]

Cox et al.

[11] 4,421,668

[45] Dec. 20, 1983

[54] BLEACH COMPOSITION

[75] Inventors: Roger B. Cox, Reading; David C. Steer; John R. Woodward, both of Wirral, all of England

[73] Assignee: Lever Brothers Company, New York, N.Y.

[21] Appl. No.: 388,797

[22] Filed: Jun. 16, 1982

[30] Foreign Application Priority Data

Jul. 7, 1981 [GB] United Kingdom ................ 8120892

[51] Int. Cl.[3] ...................... C11D 17/00; C01B 13/00; C01B 15/037; C12N 9/02

[52] U.S. Cl. ................................ 252/174.12; 252/95; 252/104; 252/186.38; 252/186.39; 252/186.40; 252/186.41; 252/186.43; 423/272; 423/584; 435/189; 435/190; 435/168; 435/264; 8/111

[58] Field of Search ..................... 252/95, 104, 174.12, 252/186.38, 186.39, 186.40, 186.41, 186.43; 423/272, 584; 435/189, 190, 168, 264; 8/111

[56] References Cited

U.S. PATENT DOCUMENTS 3,163,606 12/1964 Viveen et al. .................. 252/186.41

4,250,261 2/1981 Eggeling et al. ................... 435/190

FOREIGN PATENT DOCUMENTS 2557623 6/1977 Fed. Rep. of Germany .

1225713 3/1971 United Kingdom .

OTHER PUBLICATIONS

Barman, Enzyme Handbook, Supp. 1, 1974, pp. 70–71.

*Primary Examiner*—Mary F. Downey

*Attorney, Agent, or Firm*—Amirali Y. Haidri; James J. Farrell

[57] ABSTRACT

A liquid bleach composition comprises a hydrogen peroxide precursor which includes as an enzyme an alcohol oxidase and as a substrate for the enzyme the corresponding alcohol, the enzyme and the substrate being incapable of substantial interaction in the composition. The composition contains less than 1 unit of catalase for every 2 units of the alcohol oxidase so that peroxide formation, when the composition is diluted with 100 times its volume of water to trigger the interaction of the enzyme and its substrate, it not substantially impaired. The diluted composition has a pH value of from 7.5 to 11. Preferably, the composition also comprises detergent active compound.

20 Claims, No Drawings

BLEACH COMPOSITION

This invention relates to bleach compositions in liquid form, particularly liquid detergent compositions containing a hydrogen peroxide precursor which is stable in the composition but which is activated to yield hydrogen peroxide on dilution of the composition with water, especially at low temperatures.

Detergent compositions containing a bleaching agent such as perborate are generally only available in powder form due to the instability of the bleaching agent in aqueous liquid detergents. Powder products such as these are also difficult to disperse and dissolve efficiently in water, for example, when added to the wash cycle of a laundry operation, and in any case generally only bleach fabrics effectively when employed at a relatively high wash temperature.

Accordingly, there exists a need for a liquid detergent composition containing a bleaching agent which is stable while stored prior to use but which will bleach fabrics at a low temperature on dilution of the composition with water, for example when added to the wash cycle of a laundry operation.

It is also evident that there also exists a need for a similar composition for use in bleaching, which does not necessarily contain (a) detergent active compound(s).

It has been proposed in German patent application No. 2,557,623 to provide a liquid detergent and cleaning composition containing a $C_1$ to $C_3$ alkanol, surfactants and builders and an alcohol oxidase in tablet form which is capable of catalysing the oxidation of the alcohol in the presence of air, when added to the composition, to form hydrogen peroxide. The alcohol oxidase is obtained from yeasts such as *Candida boidinii* and Kloeckera sp or from Basidiomycetus.

It has also been proposed in British patent specification No. 1,225,713 to provide a dry powdered detergent composition comprising detergent material, builder salts, and, as a hydrogen peroxide precursor, a mixture of glucose and glucose oxidase.

It has now been discovered that a bleach composition containing a hydrogen peroxide precursor in liquid form can be prepared by mixing a specially prepared alcohol oxidase with an alcohol, the composition yielding hydrogen peroxide on dilution with water to provide a bleaching composition.

The invention accordingly provides a liquid bleach composition comprising:

a hydrogen peroxide in turn (a) as an enzyme, a $C_1$ to $C_4$ alkanol oxidase, and (b) as a substrate, a $C_1$ to $C_4$ alkanol, the enzyme and substrate being incapable of substantial interaction in the composition to form hydrogen peroxide until the composition is diluted with water;

the composition containing less than 1 unit of catalase for every 2 units of alkanol oxidase, and the composition on dilution with 100 times its volume of water having a pH value of from 7.5 to 11.

The invention also provides a liquid detergent bleach composition comprising (i) (a) detergent active compound(s);

(ii) a hydrogen peroxide precursor comprising (a) as an enzyme, a $C_1$ to $C_4$ alkanol oxidase; and (b) as a substrate, a $C_1$ to $C_4$ alkanol, the enzyme and substrate being incapable of substantial interaction in the composition to form hydrogen peroxide until the composition is diluted with water;

the composition containing less than 1 unit of catalase for every 2 units of alkanol oxidase, and the composition on dilution with 100 times its volume of water having a pH value of from 7.5 to 11.

Although the hydrogen peroxide precursor need not necessarily contain detergent active compound, a preferred embodiment of the invention is a liquid detergent bleach composition comprising, inter alia, the hydrogen peroxide precursor, the concentration of the detergent active compound being sufficiently high to prevent substantial interaction of the enzyme and substrate while the composition is stored prior to use. Accordingly, the invention will now be further described in terms of this preferred embodiment, but it is to be understood that the invention is not limited to compositions which comprise detergent active compound.

Detergent Active Compound

Detergent active compounds suitable for use in detergent compositions of the invention can be non-soap anionic or nonionic or cationic or amphoteric or zwitterionic in character. Typical non-soap anionic detergent-active compounds include water-soluble salts, particularly the alkali metal, ammonium and alkanolammonium salts, of organic sulphuric reaction products having in their molecular structure an alkyl group containing from about 8 to about 22 carbon atoms, preferably a straight chain of from 12 to 14 carbon atoms, and a sulphuric acid or sulphuric acid ester group. (Included in the term "alkyl" is the alkyl portion of acyl groups). Examples of this group of non-soap detergents which can be used are the sodium and potassium alkyl sulphates, especially those obtained by sulphating the higher alcohols ($C_8$–$C_{18}$ carbon atoms) produced by reducing the glycerides of tallow or coconut oil; and sodium and potassium alkyl benzene sulphonates, in which the alkyl group contains from about 9 to about 15 carbon atoms in straight chain or branched chain configuration.

Other non-soap anionic detergent-active compounds include the sodium alkyl glycerol ether sulphonates, especially those ethers or higher alcohols derived from tallow and coconut oil; sodium coconut oil fatty acid monoglyceride sulphonates and sulphates; and sodium or potassium salts of alkyl phenol ethylene oxide ether sulphate containing about 1 to about 10 units of ethylene oxide per molecule and wherein the alkyl groups contain from 8 to 12 carbon atoms.

Other useful non-soap anionic detergent-active compounds include the water-soluble salts of esters of alpha-sulphonated fatty acids containing from 6 to 20 carbon atoms in the ester group; water-soluble salts of 2-acyloxy-alkane-1-sulphonic acids containing from 2 to 9 carbon atoms in the acyl group and from 9 to 23 carbon atoms in the alkane moiety; alkyl ether sulphates containing from 10 to 20 carbon atoms in the alkyl group and from 1 to 30 moles of ethylene oxide; water-soluble salts of olefin sulphonates containing from 12 to 24 carbon atoms; and 6-alkoxy alkane sulphonates containing from 1 to 3 carbon atoms in the alkyl group and from 8 to 20 carbon atoms in the alkane moiety.

Preferred water-soluble non-soap anionic detergent-active compounds include linear alkyl benzene sulphonates containing from 11 to 14 carbon atoms in the alkyl group: the tallow range ($C_{12-20}$) alkyl sulphates; the coconut range alkyl glyceryl sulphonates; and alkyl ether sulphates wherein the alkyl moiety contains from 14 to 18 carbon atoms and wherein the average degree of ethoxylation varies between 1 and 6.

Specific preferred non-soap anionic detergent-active compounds include: sodium linear $C_{10}$–$C_{12}$ alkyl benzene sulphonate, triethanolamine $C_{10}$–$C_{12}$ alkyl benzene sulphonate; sodium tallow alkylsulphate; and sodium coconut alkyl glyceryl ether sulphonate; and the sodium salt of a sulphate condensation product of tallow alcohol with from 3 to 10 moles of ethylene oxide.

It is to be understood that any of the foregoing anionic detergent-active compounds can be used separately or as mixtures.

Examples of suitable nonionic detergent-active compounds are condensates of linear and branched chain aliphatic alcohols or carboxylic acids of from 8 to 18 carbon atoms with ethylene oxide, for instance a coconut alcohol-ethylene oxide condensate of 6 to 30 moles of ethylene oxide per mole of coconut alcohol; condensates of alkylphenols whose alkyl group contains from 6 to 12 carbon atoms with 5 to 25 moles of ethylene oxide per mole of alkylphenol; condensates of the reaction product of ethylenediamine and propylene oxide with ethylene oxide, the condensates containing from 40 to 80% of polyoxyethylene radicals by weight and having a molecular weight of from 5,000 to 11,000; tertiary amine oxides of structure $R_3NO$, where one group R is an alkyl group of 8 to 18 carbon atoms and the others are each methyl, ethyl or hydroxyethyl groups, for instance dimethyldodecylamine oxide; tertiary phosphine oxides of structure $R_3PO$, where one group R is an alkyl group of from 10 to 18 carbon atoms, and the others are each alkyl or hydroxyalkyl groups of 1 to 3 carbon atoms, for instance dimethyldodecylphosphine oxide; and dialkyl sulphoxides of structure $R_2SO$ where one group R is an alkyl group of from 10 to 18 carbon atoms and the other is methyl or ethyl, for instance methyltetradecyl sulphoxide.

Suitable cationic detergent-active compounds are quaternary ammonium salts having an aliphatic radical of from 8 to 18 carbon atoms, for instance cetyltrimethyl ammonium bromide.

Examples of suitable amphoteric detergent-active compounds are derivatives of aliphatic secondary and tertiary amines containing an alkyl group of 8 to 18 carbon atoms and an aliphatic radical substituted by an anionic water-solubilising group, for instance sodium 3-dodecylaminopropionate, sodium 3-dodecylaminopropane sulphonate and sodium N-2-hydroxydodecyl-N-methyltaurate.

Suitable zwitterionic detergent-active compounds are derivatives of aliphatic quaternary ammonium, sulphonium and phosphonium compounds having an aliphatic radical of from 8 to 18 carbon atoms and an aliphatic radical substituted by an anionic water-solubilising group, for instance 3-(N,N-dimethyl-N-hexadecylammonium)propane-1-sulphonate betaine and 3-(cetylmethylphosphonium)ethane sulphonate betaine.

In addition to any of the above non-soap detergent-active compounds, soaps can optionally also be present. Soaps are salts of fatty acids and include alkali metal soaps such as the sodium, potassium, ammonium and alkanol ammonium salts of higher fatty acids containing from 8 to 24 carbon atoms, and preferably from 10 to 20 carbon atoms. Particularly useful are the sodium and potassium and mono-, di- and triethanolamine salts of the mixtures of fatty acids derived from coconut oil and tallow. Further examples of detergent-active compounds are compounds commonly used as surface-active agents listed in the well-known textbooks "Surface Active Agents", Volume 1 by Schwartz and Perry and "Surface Active Agents and Detergents", Volume II by Schwartz, Perry and Berch.

The amount of detergent-active compound to be incorporated into detergent compositions according to the invention is from 1 to 90% by weight. The preferred amount forms from 5 to 80%, most preferably from 10 to 70% by weight of the composition.

The amount of detergent active compound to be employed can also be sufficiently high to ensure that the enzyme and substrate which comprise the hydrogen peroxide precursor are incapable of substantial interaction while the composition is stored prior to use, for example in a laundry operation. For this purpose, the composition should accordingly comprise at least 7%, preferably 8 to 90% by weight of detergent active compound, the amount of available water in the composition being insufficient to enable enzyme and substrate to interact. It is to be understood, however, that the hydrogen peroxide precursor can alternatively be maintained in an inactive state in the liquid detergent composition by reliance on means other than the presence of detergent active compound at a sufficiently high concentration.

The Hydrogen Peroxide Precursor

The hydrogen peroxide precursor comprises, as an enzyme, a $C_1$ to $C_4$ alkanol oxidase and, as a substrate, a $C_1$ to $C_4$ alkanol. The enzyme can be non-specific in that under suitable conditions, it will interact with any $C_1$ to $C_4$ alkanol, or it can be specific in that it will interact with only one or two $C_1$ to $C_4$ alkanols.

The $C_1$ to $C_4$ alkanol oxidase can conveniently be obtained as a by-product of the growth of a suitable microorganism in a suitable culture medium. A suitable organism for this purpose is a yeast.

By way of illustration, the preparation of alcohol oxidase by culturing a species of a yeast of the genus Hansenula will now be described. It is to be understood, however, that the invention is not limited to the use of this particular genus of yeast, for the production of alcohol oxidase.

*Hansenula polymorpha* (ATCC 26012) was grown in batch culture at pH 5.5 at a temperature of 40° C. in a medium containing the following ingredients including methanol as the sole source of carbon:

| | |
|---|---|
| Ammonium sulphate | 1.5 g |
| Potassium dihydrogenphosphate | 1.0 g |
| Magnesium sulphate, heptahydrate | 0.2 g |
| Sodium chloride | 0.1 g |
| Mineral salts solution (trace metals) | 1.0 ml |
| Biotin | 5 μg |
| Thiamine hydrochloride | 300 μg |
| Methanol | 5 g |
| Water | to 1000 ml |

*Hansenula polymorpha* (ATCC 26012) was also grown by continuous culture at a pH maintained between 5 and 5.5 and at a temperature of 40° C., in a medium containing the following ingredients, including methanol as the sole source of carbon:

| | |
|---|---|
| Ammonium sulphate | 4.0 g |
| Potassium dihydrogen phosphate | 2.0 g |
| Magnesium sulphate, heptahydrate | 0.3 g |
| Sodium chloride | 0.2 g |

-continued

| | | |
|---|---|---|
| Biotin | 5 | μg |
| Thiamine hydrochloride | 300.0 | μg |
| Mineral salts solution (trace metals) | 1.0 | ml |
| Methanol | 25 | g |
| Water | to 1000 | ml |

Cells from both cultures were harvested by centrifugation, disintegrated and a cell-free extract obtained in a 100 mM phosphate buffer at pH 7.8.

Alcohol oxidase present in this cell-free extract was assayed according to the method of Tani et al, Agr.Biol. Chem. 36 (1): 68–75 (1972).

In this method, 0.1 ml of suitably diluted extract was incubated with 20μ moles of methanol, and 150μ moles of phosphate buffer (pH 7.4) in a total volume of 1.3 ml for 15 minutes at 37° C. The reaction was stopped by the addition of 0.2 mls of 4 M HCl. A blank was set up for each assay replacing methanol with distilled water, and adding acid prior to incubation. The formaldehyde produced was then measured by incubating the reaction mixture with 1.5 ml Nash reagent (2 M ammonium acetate, 0.05 M acetic acid, 0.02 M acetyl acetone in water) and measuring the absorbance at 412 nm against the corresponding blank.

Catalase is also usually present in the cell-free extract and this will reduce the apparent ability of alcohol oxidase to produce hydrogen peroxide by interaction with methanol, by reduction of the hydrogen peroxide as it is formed. It is accordingly advantageous to measure the amount of catalase which contaminates the alcohol oxidase present in the cell free extract.

Catalase was measured spectrophotometrically by the method of Luck "Methods in Enzymatic Analysis" (Ed. Bergmoyer) pp 885–894 (1963): The decrease in $E_{240}$ was measured at room temperature as 0.1 ml of extract was added to 38μ moles of $H_2O_2$ and 200μ moles of phosphate buffer (pH 7.8) in a total volume of 2.0 ml.

One unit of enzyme activity is defined as that quantity required to convert 1μ mole of substrate per minute under standard assay conditions.

It is an important aspect of the invention to provide a source of alcohol oxidase which contains insufficient catalase to interfere with the generation of hydrogen peroxide so that soiled fabric, such as standard tea stained cloth, can be bleached efficiently on dilution of the composition with water.

Accordingly, the composition should preferably contain no more than 1 unit of catalase for every 2 units of alcohol oxidase. Preferably, the composition should contain less than 1 unit of catalase for every 10 units of alcohol oxidase, and most preferably less than 1 unit of catalase for every 100 units of alcohol oxidase. Ideally, the composition is substantially free from catalase.

One method for separating catalase from a cell free extract containing alcohol oxidase prepared as described hereinbefore, includes the separation of the oxidase and catalase using column chromatography.

By way of illustration, a suitable method of separation can be carried out as follows:

500 ml of pre-swollen DEAE sephacel, suspended in 25% alcohol is filtered under vacuum and resuspended in fresh phosphate buffer at pH 7.8. This operation is repeated until the pH of the filtrate matches the starting buffer (usually 4–5 washings).

Cell-free extract, prepared as hereinbefore described and containing at least 300 units of catalase for each unit of alcohol oxidase, is carefully stirred into a suitable quantity of the DEAE-sephacel so prepared, and the mixture poured into a column. The column is then eluted with buffer until the catalase activity in the eluant is negligible; under these conditions the alcohol oxidase remains adsorbed on the sephacel. On increasing the ionic strength of the eluting buffer, by addition of 5% NaCl, the alcohol oxidase is then eluted from the column. The eluant so obtained contains no more than 1 unit of catalase for every 10 units of oxidase. For storage until required for use in detergent compositions, the oxidase can be precipitated from the eluant using 70% ammonium sulphate, and separated by centrifugation at 50,000×g.

It is also possible to reduce the amount of catalase which normally contaminates the source of alcohol oxidase such as *Hansenula polymorpha,* as herein described, by treatment of the disintegrated yeast cells with an anionic non-soap detergent having a straight chain of from 12 to 14 carbon atoms. Examples of suitable anionic detergents for this purpose are sodium lauryl sulphate and sodium dodecyl benzene sulphonate.

According to a preferred procedure for reducing or eliminating catalase by this method, cells of *Hansenula polymorpha* grown on a methanol containing medium, such as hereinbefore described, are disintegrated and contacted with an anionic detergent such as sodium lauryl sulphate at a concentration of from 1 to 2% by weight. The duration of contact can be up to one hour and the temperature of contact can be 15° to 50° C., preferably 25° to 40° C. The supernatant obtained after separation of cell debris and any sedimented detergent will contain little or no catalase activity, whereas alcohol oxidase activity will be substantially unimpaired.

It is also possible to provide a source of alcohol oxidase which is substantially free from catalase by culturing a yeast which is incapable of producing catalase. Such a yeast can be obtained for example by selecting a strain of the yeast, *Saccharomyces cerevisiae* which is known for its inability to produce catalase, and introducing into that strain genetic material, taken from cells of *Hansenula polymorpha,* which is responsible for the production of alcohol oxidase. The genetically modified strain of *Saccharomyces cerevisiae* will then be capable of producing cells yielding alcohol oxidase which is free from catalase.

The quantity of alcohol oxidase to be employed in compositions according to the invention should be at least sufficient to provide, after dilution of the composition with water and interaction with the alcohol, sufficient hydrogen peroxide to bleach standard tea stained fabric.

A sufficient amount of alcohol oxidase will depend on its activity and the activity of any residual catalase that may be present, but by way of example it can be stated generally that the detergent composition according to the invention will contain from 50 to 1000, preferably from 100 to 500 units alcohol oxidase per ml of the detergent composition. When the composition is then diluted 100 times by addition to water to provide a medium suitable for washing and bleaching fabrics, the medium will contain from 0.5 to 10, preferably from 1 to 5 units of enzyme per ml which on interaction with the alcohol substrate also present will produce sufficient hydrogen peroxide to bleach standard tea stained fabric.

The hydrogen peroxide precursor also comprises, as a substrate for the enzyme, a $C_1$ to $C_4$ alkanol, examples of which are methanol, ethanol, n-propanol, and n-butanol. The preferred alkanol is ethanol.

The quantity of the alcohol to be employed should be at least sufficient to provide, after dilution of the composition with water and interaction with the alcohol oxidase, sufficient hydrogen peroxide to bleach standard tea stained fabric. A suitable quantity of alcohol forms from 5 to 25%, preferably 5 to 20% and most preferably 5 to 12% by weight of the composition.

The quantity of hydrogen peroxide precursor containing alcohol oxidase and the alcohol in the composition, which is sufficient on dilution of the composition with water to bleach standard tea stained fabric, should be such that when the composition is diluted with 100 times its weight of water, the enzyme and substrate will react, at a temperature of 40° C. and a pH of 9 to yield hydrogen peroxide at a concentration of at least 5 mM. Preferably, the alcohol oxidase and the alcohol are present in sufficient quantity to yield under these conditions hydrogen peroxide at a concentration of at least 8 mM, most preferably 20 mM or even higher.

It can be stated generally that the composition on dilution with 100 times its own weight of water will yield a solution having a pH value of from 7.5 to 11, preferably 8.5 to 10.5, most preferably from 8.5 to 10. Should the resultant pH value of the diluted composition be less than pH 7.5, then bleaching is likely to be inefficient even at temperatures of up to 100° C. If on the other hand the pH value of the diluted composition exceeds 11, then it is unlikely to be suited to the washing and bleaching of fabric, such as the domestic laundering of soiled clothing. It is also possible that the activity of the alcohol oxidase in generating hydrogen peroxide may be impaired by subjecting it to an environment where the pH value is greater than pH 11.

The ability of the alcohol oxidase to generate hydrogen peroxide can be assessed by measuring the concentration formed in a well aerated system containing pH 9 buffer (1000μ moles) and the alcohol (200μ moles) in a total volume of 10 ml at 37° C. The peroxide concentration can be determined by stopping the reaction after a standard time by the addition of 10 ml of 10% w/v sulphuric acid and titrating with potassium permanganate.

The hydrogen peroxide precursor should be stabilised in the detergent composition in such a manner that the enzyme and substrate are incapable of substantial interaction, otherwise the ability of the composition to provide bleaching action when diluted with water might well be lost or may have diminished during storage to an unacceptable level.

The enzyme and substrate can, for example, be temporarily prevented from interacting to form hydrogen peroxide by dissociating the enzyme, for instance by ensuring that the composition contains a sufficiently high concentration of detergent active compound to reduce the availability of water, it being understood that the enzyme can be activated to then interact with the substrate when the concentration of the detergent active compound is reduced on dilution with water.

The enzyme can also be temporarily inactivated by dissociation, by reducing the availability of water in the composition by other means, either by excluding water altogether or by reducing the water activity ($\alpha_w$) of the composition. The $\alpha_w$ of the composition can for example be reduced below 1.00 by the presence in solution of the alcohol, salts, glycerol and other electrolytes.

Alternatively, it is also possible to stabilise the hydrogen peroxide precursor by other means, such as by encapsulation of the alcohol oxidase in a manner such that the alcohol oxidase is released on dilution of the composition with water, or by precipitation of the alcohol oxidase with a salt such as ammonium sulphate, whose salting out effect is lost on dilution with water and resolution of the alcohol oxidase, or by maintaining the hydrogen peroxide precursor substantially free from oxygen, for example by employing an antioxidant such as ascorbic acid, so that the enzyme and substrate cannot react to form hydrogen peroxide.

Bleach Activators

Compositions according to the invention will also preferably contain a bleach activator to enable hydrogen peroxide generated at a low temperature of for example from 15°-55° C. to bleach soiled fabric.

Bleach activators are conventionally organic compounds having one or more acyl reactive acyl residues, which at relatively low temperatures react with hydrogen peroxide causing the formation of organic peracids, the latter providing for a more effective bleaching action at lower temperatures than hydrogen peroxide itself. The best known organic activator of practical importance is N,N,N',N'-tetraacetyl ethylenediamine, normally referred to as simply tetraacetyl ethylenediamine and coded TAED.

Examples of other organic bleach activators are other N-acyl substituted amides, for example tetraacetyl methylene diamine, carboxylic acid anhydrides, for example succinic, benzoic and phthalic anhydrides; carboxylic acid esters, for example sodium acetoxy benzene sulphonate, sodium p-sulphonated phenyl benzoate; acetates, such as glucose pentaacetate and xylose tetraacetate, and acetyl salicylic acid.

Organic bleach activators can be employed in compositions according to the invention at a concentration of from 0.1 to 10%, preferably from 0.5 to 5% by weight.

It is also possible to use as bleach activators heavy metal ions of the transition series, such as cobalt, which catalyse peroxide decomposition, optionally together with a special type of chelating agent for said heavy metal such as are described in U.S. Pat. No. 3,156,654.

Detergency Builders other than Soap

The compositions according to the invention can also contain detergency builders.

Useful builders include inorganic and organic water-soluble builder salts, as well as various water-insoluble and so-called "seeded" builders.

Inorganic detergency builders include, for example, water-soluble salts of phosphates, pyrophosphates, orthophosphates, polyphosphates, phosphonates, carbonates, bicarbonates, borates and silicates. Specific examples of inorganic phosphate builders include sodium and potassium tripolyphosphates, phosphates and hexametaphosphates. The polyphosphonates specifically include, for example, the sodium and potassium salts of ethylene diphosphonic acid, the sodium and potassium salts of ethane 1-hydroxy-1,1-diphosphonic acid, and the sodium and potassium salts of ethane-1,1,2-triphosphonic acid. Sodium tripolyphosphate is an especially preferred water-soluble inorganic builder.

Non-phosphorus containing sequestrants can also be selected for use as detergency builders. Specific examples of non-phosphorus, inorganic builder ingredients include water-soluble inorganic carbonate, bicarbonate, borate and silicate salts. The alkali metal, e.g. sodium and potassium, carbonates, bicarbonates, borates (Borax) and silicates are particularly useful.

Water-soluble, non-phosphorus organic builders are also useful. For example, the alkali metal, ammonium and substituted ammonium polyacetates, carboxylates, polycarboxylates, succinates, and polyhydroxysulphonates are useful builders in the present compositions and processes. Specific examples of the polyacetate and polycarboxylate builder salts include sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid.

Highly preferred non-phosphorous builder materials (both organic and inorganic) include sodium carbonate, sodium bicarbonate, sodium silicate, sodium citrate, sodium oxydisuccinate, sodium mellitate, sodium nitrilotriacetate, and sodium ethylenediaminetetraacetate, carboxymethoxysuccinate, carboxymethoxymalonate and mixtures thereof.

Another type of detergency builder material useful in the compositions of the invention comprises a water-soluble material capable of forming a water-insoluble reaction product with water hardness cations in combination with a crystallisation seed which is capable of providing growth sites for said reaction product.

Specific examples of materials capable of forming the water-insoluble reaction product include the water-soluble salts of carbonates, bicarbonates, sesquicarbonates, silicates, aluminates and oxalates. The alkali metal, especially sodium salts of the foregoing materials are preferred for convenience and economy.

Yet another class of detergency builder materials useful in the compositions of the invention are zeolites.

The detergency builder component when present will generally comprise from 2 to 50%, preferably from 5 to 40% by weight of the detergent composition.

Suspending Agents

Suspending agents can be employed in compositions according to the invention to prevent insoluble material, for example the enzyme if in a salted out state, from settling out during storage of the composition prior to use.

Examples of suspending agents are a polyacrylic acid polyalkyl sucrose ether cross-linked copolymer, such as CARBOPOL, which can be employed at a concentration of from 0.8 to 1.5%, xanthan gum, such as KELZAN, which can be employed at a concentration of from 0.25 to 1% and the heteropolysaccharide, BIOPOLYMER PS 87 (as described in published European Patent Application No. 80302307.6, publication No 0 023 397), which can be employed at a concentration of 0.2 to 0.5%.

Other Detergent Adjuncts

Other detergent adjuncts that can optionally be present in compositions according to the invention include sequestrants, super-fatting agents, such as free long-chain fatty acids, lather boosters, such as coconut monoethanolamide; lather controllers; inorganic salts such as sodium and magnesium sulphates; moisturisers; plasticiers and anti-caking agents; antiredeposition agents; soil-release agents; filler materials; optical brighteners; anti-spotting agents; dyes; opacifiers, colourants, fluorescers, perfumes, germicides and other deodorant materials such as zinc ricinoleate; and water.

In addition to alcohol oxidases, various other detergency enzymes well-known in the art for their ability to degrade and aid in the removal of various soils and stains can also optionally be employed in compositions according to this invention. Detergency enzymes are commonly used at concentrations of from about 0.1% to about 1.0% by weight of such compositions. Typical enzymes include the various proteases, lipases, amylases, and mixtures thereof, which are designed to remove a variety of soils and stains from fabrics.

The total amount of detergent adjuncts that can be incorporated into the detergent composition according to the invention will normally form the balance of the composition after accounting for the detergent-active compound and hydrogen peroxide precursor. The detergent adjuncts will accordingly form from 1 to 98% by weight of the product.

Product Type and Formulation

The detergent composition of the invention is in the form of a liquid detergent active compound comprising the hydrogen peroxide precursor, and optionally a bleach activator and other ingredients.

The detergent composition is preferably thickened to facilitate dispensing it, for example, when added to a washing machine as part of a laundry process.

The composition according to the invention can also be substantially free from detergent active compound and can be used, for example, as a liquid bleach product in the prebleaching of soiled garments preparatory to laundering with a conventional detergent composition, or in the bleaching of hard surfaces such as a lavatory bowl, basin, sink or bath after suitably diluting it with water in order to enable the enzyme and substrate to interact and bleaching to proceed.

It is to be understood that the composition of the invention is liquid in the sense that it can normally be poured or squeezed from a container as a free flowing liquid. Some of the ingredients of the composition may however be in the form of finely divided solids having a particle size which does not usually exceed 200 microns, in which case, it will usually be necessary to include in the composition a suspending agent to ensure that such solids are uniformly distributed.

Process for Preparing Liquid Detergent Compositions

The invention also provides a process for preparing a liquid detergent composition which comprises the steps of:

(i) preparing a mixture in liquid form of detergent active compound, a $C_1$ to $C_4$ alkanol and a bleach activator, and (ii) subsequently adding to this mixture a $C_1$ to $C_4$ alkanol oxidase, the alkanol oxidase and alkanol being incapable of substantial interaction in the composition so formed to form hydrogen peroxide until the composition is diluted with water; the composition containing less than 1 unit of catalase for every 2 units of alkanol oxidase; and the composition on dilution with 100 times its volume of water having a pH value of from 7.5 to 11.

The process for preparing liquid detergent compositions accordingly comprises dissolving or dispersing in a liquid detergent-active compound, together with a bleach activator and, if desired, other detergent adjuncts, sufficient of the alcohol which comprises the enzyme substrate of the hydrogen peroxide precursor to provide a liquid detergent composition to which is subsequently added the alkanol oxidase which comprises the enzyme of the hydrogen peroxide precursor. It is desirable to add the enzyme to the remainder of the detergent composition at a stage towards the end of its manufacture, to minimise loss of enzyme activity, such as may occur during a heating step, or due to premature interaction of the enzyme and substrate.

Methods of Using the Composition

The detergent composition of the invention is to be employed particularly in the bleaching and laundering of soiled garments, preferably at a wash temperature of from 15° C. to 55° C.

In use, the detergent composition, when employed as a fabric washing product, can for example be applied to a garment according to conventional laundering procedures involving water washing, rinsing and drying, in which case it will usually be diluted with at least 100 times its volume of water.

The invention is illustrated by the following Examples in which Examples 1 to 10 are to detergent bleach compositions, each of which containing a sufficiently high concentration of detergent active compound to ensure that the hydrogen peroxide precursor remains inactive until the compositions are diluted with water.

EXAMPLE 1

This example illustrates a liquid detergent composition according to the invention and provides data to indicate that the composition can be employed to bleach stained fabric.

The detergent composition had the following formulation:

| | % w/w |
|---|---|
| Detergent active compound | |
| Sodium lauryl ether sulphate (28% AD) | 30 |
| Substrate | |
| Methanol | 15 |
| Builder | |
| Sodium tripolyphosphate | 15 |
| Bleach activator | |
| TAED | 2 |
| Water | to 100 |

Enzyme

Alcohol oxidase: 500 units/ml of the total detergent composition (containing approximately 1 unit catalase to 10 units oxidase)

Bleaching Test 5 cm×5 cm squares of standard tea stained fabric (BCl) were placed in 50 ml of pH 9 buffer containing 0.5 g of the liquid detergent bleach composition. This represents a dilution of 1 part of the composition in 100 parts of water. Air was bubbled through the liquid for 20 minutes at a temperature of 40° C.

The fabric squares were then removed from the liquid, rinsed with water, dried and pressed, and the reflectance measured using a Zeiss photometer at 460 nm with a 420 nm UV interference filter. The reflectance values obtained were compared with values obtained using pieces of untreated BCl fabric. An increase in the reflectance value was indicative of bleaching. Values were therefore recorded as differences ($\Delta R_{460}$) between treated and untreated BCl fabric.

Results

In this Example, a $\Delta R_{460}$ value of 4 was obtained. This represents a satisfactory bleach. In a control experiment where similar pieces of BCl fabric were treated with the above formulation but without the enzyme, no change in reflectance was observed.

EXAMPLE 2

In this Example, a liquid detergent bleach composition having the following formulation was prepared.

| | % w/w |
|---|---|
| sodium lauryl ether sulphate (28% AD) | 30 |
| sodium N—lauroyl sarcosinate (97% AD) | 4 |
| polyethylene glycol 400 | 1 |
| cetyl alcohol | 1 |
| TAED | 2 |
| ethanol | 15 |
| water | to 100 |
| alcohol oxidase (280 units/ml) | |

This formulation contained less than 1 unit catalase for every 10 units oxidase.

The ability of this formulation to bleach standard BCl fabric was tested by the method described in Example 1. The results obtained were as follows.

| Wash or wash + bleach at pH 9/40° C. | $\Delta R_{460}$ |
|---|---|
| control (no enzyme) wash for 60 minutes | 0.2 |
| wash/bleach for 30 minutes | 1.2 |
| wash/bleach for 60 minutes | 3.6 |

This represented a satisfactory bleach.

EXAMPLE 3

In this Example, a liquid detergent bleach composition having the following formulation was prepared:

| | % w/w |
|---|---|
| alkyl $C_{12}$ to $C_{15}$ ethoxylated | 8 |
| alcohol (9$\overline{EO}$) | |
| sodium xylene sulphonate (30% AD) | 6 |
| sodium pyrophosphate | 2.8 |
| potassium pyrophosphate | 22 |
| sodium silicate | 3 |
| sodium carboxymethyl cellulose | 0.38 |
| fluorescer | 0.1 |
| TAED | 5 |
| ethanol | 10 |
| water | to 100 |
| alcohol oxidase (280 units/ml) | |

This formulation contained less than 1 unit catalase for every 10 units oxidase.

The ability of this formulation to bleach standard BCl fabric was tested by the method described in Example 1. The results were as follows:

| Wash or wash + bleach at pH 9.0/40° C. | $\Delta R_{460}$ |
|---|---|
| control (no enzyme) wash for 60 minutes | 0.3 |
| wash/bleach for 30 minutes | 4.9 |

-continued

| Wash or wash + bleach at pH 9.0/40° C. | $\Delta R_{460}$ |
|---|---|
| wash/bleach for 60 minutes | 8.4 |

This represented a satisfactory bleach.

EXAMPLE 4

In this Example, a liquid detergent bleach composition having the following formulation was prepared:

| | % w/w |
|---|---|
| synthetic primary alcohol ethylene oxide condensate (SYNPERONIC K87) | 8 |
| glycerol | 10 |
| borax | 8 |
| sodium tripolyphosphate | 10 |
| sodium acetoxy benzene sulphonate (SABS) | 3 |
| ethanol | 8 |
| water | to 100 |
| alcohol oxidase (280 units/ml) | |

This formulation contained less than 1 unit catalase for every 10 units oxidase.

The ability of this formulation to bleach standard BCl fabric was tested by the method described in Example 1.

| wash or wash + bleach at pH 9.0/40° C. | $\Delta R_{460}$ |
|---|---|
| control (no enzyme) wash for 60 minutes | 0.5 |
| wash/bleach for 30 mintues | 3.8 |
| wash/bleach for 60 minutes | 5.1 |

This represents a satisfactory bleach.

EXAMPLE 5

In this Example, the effect using different bleach activators is compared. For this purpose a liquid detergent bleach base composition was prepared without added bleach activator. This base composition had the following formulation:

| | % w/w |
|---|---|
| sodium lauryl sulphate | 1.5 |
| SYNPERONIC K87 | 10 |
| sodium tripolyphosphate | 15 |
| glycerol | 8 |
| borax | 6 |
| heteropolysaccharide thickener (Biopolymer PS 87) | 0.275 |
| ethanol | 10 |
| water | to 100 |
| alcohol oxidase (280 units/ml) | |

This formulation contained less than 1 unit catalase for every 10 units oxidase.

The ability of this formulation, with three different bleach activators, to bleach standard BCl fabric was tested by the method described in Example 1. The results obtained were as follows:

| Treatment | % w/w | wash or wash/bleach time (mins) at pH 8.5/37° C. | $\Delta R_{460}$ |
|---|---|---|---|
| control (no enzyme, no bleach activator) | 0 | 60 | 1.1 |

-continued

| Treatment | % w/w | wash or wash/bleach time (mins) at pH 8.5/37° C. | $\Delta R_{460}$ |
|---|---|---|---|
| TAED | 4 | 30 | 5.5 |
| glucose pentaacetate | 5 | 30 | 4.5 |
| | | 60 | 6.7 |
| xylose tetraacetate | 5 | 30 | 4.8 |

All these results indicate that each of the three bleach activators provides for a satisfactory bleach.

EXAMPLE 6

In this Example, a liquid detergent bleach composition having the following formulation was prepared:

| | % w/w |
|---|---|
| dodecylbenzene sulphonate | 5 |
| SYNPERONIC K87 | 2 |
| sodium tripolyphosphate | 21 |
| glycerol | 10 |
| borax | 7 |
| fluorescer | 0.1 |
| suspending agent (CARBOPOL 941) | 1 |
| TAED | 4 |
| ethanol | 8 |
| water | to 100 |
| alcohol oxidase (280 units/ml) | |

This formulation contained less than 1 unit catalase for every 10 units oxidase.

The ability of this composition to bleach standard BCl fabric was compared with a similar formulation from which the bleach activator (TAED) had been omitted. The method employed was otherwise as described in Example 1. The results obtained were as follows:

| Treatment at pH 8.7/40° C. | $\Delta R_{460}$ |
|---|---|
| enzyme + ethanol (without TAED) 30 minutes | 1.15 |
| enzyme + ethanol + TAED 30 minutes | 6.10 |
| enzyme + ethanol + TAED 60 minutes | 12.4 |

The latter two results indicate that a very good bleach can be obtained in the presence of TAED at a low temperature. The first result without TAED represents a poor bleach and underlines the necessity for employing a bleach activator when bleaching at a low temperature.

EXAMPLE 7

This Example compares the use of methanol or ethanol as substrates and the use of TAED or sodium acetoxybenzene sulphonate (SABS) or a transition metal ion as bleach activators.

The formulation employed was as follows:

| | % w/w |
|---|---|
| dodecylbenzene sulphonate | 15.5 |
| nonionic detergent | 2.8 |
| sodium tripolyphosphate | 6.6 |
| sodium silicate | 1 |
| EDTA | 0.05 |
| sodium sulphate | 8.1 |
| CARBOPOL | 1 |
| ethanol or methanol | 8 |
| Water | to 100 |

-continued

| | % w/w |
|---|---|
| alcohol oxidase (280 units/ml) | |

This formulation contained less than 1 unit catalase for every 10 units oxidase.

The ability of this composition to bleach standard BCl fabric was tested according to the method described in Example 1 using either of the substrate alcohols and each of the bleach activators at the levels shown in the table below, which also records the bleach values obtained in each case.

| Treatment at pH 10/40° C./30 minutes | $\Delta R_{460}$ |
|---|---|
| enzyme + methanol | 0.7 |
| enzyme + methanol + transition metal ion (0.1% w/w) | 5.3 |
| enzyme + ethanol | 0.4 |
| enzyme + ethanol + transition metal ion (0.1% w/w) | 5.3 |
| enzyme + ethanol + TAED (3% w/w) | 6.1 |
| enzyme + ethanol + SABS (3% w/w) | 5.3 |

These results confirm the importance of employing a bleach activator when bleaching at a low temperature. The three bleach activators used were approximately equivalent in effectiveness in this respect. Methanol provides a suitable substrate for the oxidase which is as effective as ethanol, so far as the ability to bleach is concerned.

EXAMPLE 8

In this Example, a liquid detergent bleach composition can be prepared by employing the formulation described in Example 3, except that n-propanol (15% by weight) replaces ethanol (10% by weight).

EXAMPLE 9

In this Example, a liquid detergent bleach composition can be prepared by employing the formulation described in Example 4, except that n-butanol (10% by weight) replaces ethanol (8% by weight).

EXAMPLE 10

In this Example, a liquid detergent bleach composition can be prepared by emloying the formulation described in Example 5, except that methanol (15% by weight) replaces ethanol (10% by weight).

EXAMPLE 11

This example illustrates a liquid bleach composition which is substantially free from detergent active compound.

The liquid bleach composition had the following formulation:

| | % w/w |
|---|---|
| Substrate | |
| Ethanol | 25 |
| Bleach activator | |
| Glucose pentaacetate | 5 |
| Electrolyte (to stabilize enzyme) | |
| Sodium chloride | 15 |
| Glycerol | 40 |
| Water | to 100 |
| Enzyme | |
| Alcohol oxidase (500 units/ml) | |

This liquid bleach composition can be employed as a lavatory bleach by dispensing a volume of 50 ml into contact with the water filled s-bend trap of a lavatory bowl without flushing. Contact of the diluted bleach composition with the lavatory bowl overnight should be sufficient to effect efficient bleaching of the surface of the s-bend trap and sterilization of that surface.

What is claimed is:

1. An aqueous liquid bleach composition comprising a hydrogen peroxide precursor comprising (a) from 50 to 1000 units per ml of the composition of a $C_1$ to $C_4$ alkanol oxidase enzyme, and (b) from 5 to 25% by weight of the composition of a $C_1$ to $C_4$ alkanol substrate;

the enzyme and substrate being incapable of substantial interaction in the composition to form hydrogen peroxide until the composition is diluted with water; the composition containing less than 1 unit of catalase for every 2 units of alkanol oxidase; and the composition on dilution with 100 times its volume of water having a pH value of from 7.5 to 11.

2. The composition according to claim 1, wherein the enzyme is selected from the group consisting of methanol oxidase, ethanol oxidase, n-propanol oxidase, n-butanol oxidase and mixtures thereof.

3. The composition according to claim 1, wherein the substrate is selected from the group consisting of methanol, ethanol, n-propanol, n-butanol and mixtures thereof.

4. The composition according to claim 1, which comprises from 100 to 500 units of the enzyme per ml of the composition.

5. The composition according to claim 1, which comprises less than 1 unit of catalase for every 10 units of alkanol oxidase.

6. The composition according to claim 5, which comprises less than 1 unit of catalase for every 100 units of alkanol oxidase.

7. The composition according to claim 6, which is substantially free from catalase.

8. The composition according to claim 1, wherein the substrate forms from 5 to 20% by weight of the composition.

9. The composition according to claim 1, which on dilution with 100 times its weight of water at a temperature of 40° C. and at a pH value of 9 yields hydrogen peroxide at a concentration of at least 5 mM.

10. The composition according to claim 1, which further comprises a suspending agent.

11. The composition according to claim 1, which additionally comprises a bleach activator.

12. The composition according to claim 11, wherein the bleach activator is an organic bleach activator selected from the group consisting of N,N,N',N'-tetraacetyl ethylenediamine, N,N,N',N'-tetraacetyl methylenediamine, succinic anhydride, benzoic anhydride, phthalic anhydride, sodium acetoxybenzene sulphonate, sodium p-sulphonated phenyl benzoate, glucose pentaacetate, xylose tetraacetate, acetyl salicylic acid and mixtures thereof.

13. The composition according to claim 11, wherein the bleach activator is a heavy metal ion of the transition series.

14. The composition according to claim 12, wherein the organic bleach activator forms from 0.1 to 10% by weight of the composition.

15. The composition according to claim 1, further comprising detergent active compound.

16. The composition according to claim 15, wherein the detergent active compound forms from 1 to 90% by weight of the composition.

17. The composition according to claim 15 which further comprises a builder.

18. A process for preparing a composition according to claim 1, which process comprises the steps of (i) preparing a mixture in liquid form of a $C_1$ to $C_4$ alkanol and a bleach activator, and (ii) subsequently adding to this mixture a $C_1$ to $C_4$ alkanol oxidase, the alkanol oxidase and the alkanol being incapable of substantial interaction in the composition so formed to form hydrogen peroxide until the composition is diluted with water;

the composition containing less than 1 unit of catalase for every 2 units of alkanol oxidase; and the composition on dilution with 100 times its volume of water having a pH value of from 7.5 to 11.

19. An aqueous liquid detergent bleach composition which comprises (i) from 1 to 90% by weight of detergent active compound;

(ii) a hydrogen peroxide precursor comprising (a) from 50 to 1000 units of ethanol oxidase per ml of the composition; and (b) from 5 to 25% by weight of ethanol;

the ethanol oxidase and ethanol being incapable of substantial interaction in the composition to form hydrogen peroxide until the composition is diluted with water, and (iii) from 0.1 to 10% by weight of organic bleach activator;

the composition containing less than 1 unit of catalase for every 2 units of ethanol oxidase; and the composition on dilution with 100 times its volume of water having a pH value of from 7.5 to 11.

20. An aqueous liquid detergent bleach composition which comprises (i) from 1 to 90% by weight of detergent active compound;

(ii) a hydrogen peroxide precursor comprising (a) from 50 to 1000 units of ethanol oxidase per ml of the composition; and (b) from 5 to 25% by weight of ethanol;

the ethanol oxidase and ethanol being incapable of substantial interaction in the composition to form hydrogen peroxide until the composition is diluted with water; and (iii) a source of heavy metal ions of the transition series;

the composition containing less than 1 unit of catalase for every 2 units of ethanol oxidase; and the composition on dilution with 100 times its volume of water having a pH value of from 7.5 to 11.

* * * * *